United States Patent
Yang

(10) Patent No.: US 11,721,015 B2
(45) Date of Patent: Aug. 8, 2023

(54) DATA PROCESSING METHOD, EQUIPMENT AND STORAGE MEDIUM

(71) Applicant: ALIBABA GROUP HOLDING LIMITED, Grand Cayman (KY)

(72) Inventor: Han Yang, Hangzhou (CN)

(73) Assignee: ALIBABA GROUP HOLDING LIMITED, George Town (KY)

( * ) Notice: Subject to any disclaimer, the term of this patent is extended or adjusted under 35 U.S.C. 154(b) by 206 days.

(21) Appl. No.: 17/128,237

(22) Filed: Dec. 21, 2020

(65) Prior Publication Data

US 2021/0201481 A1 Jul. 1, 2021

(30) Foreign Application Priority Data

Dec. 25, 2019 (CN) .......................... 201911357874.1

(51) Int. Cl.
| | |
|---|---|
| *G16H 30/20* | (2018.01) |
| *G06T 7/33* | (2017.01) |
| *G06T 7/00* | (2017.01) |
| *G06N 3/08* | (2023.01) |

(52) U.S. Cl.
CPC ............. *G06T 7/0012* (2013.01); *G06N 3/08* (2013.01); *G06T 7/344* (2017.01); *G16H 30/20* (2018.01); *G06T 2207/10072* (2013.01)

(58) Field of Classification Search
None
See application file for complete search history.

(56) References Cited

U.S. PATENT DOCUMENTS

| | | | |
|---|---|---|---|
| 6,875,578 B2 | 4/2005 | Giuliano et al. | |
| 6,973,158 B2 | 12/2005 | Besson | |
| 8,351,675 B2 | 1/2013 | So et al. | |
| 8,781,193 B2 * | 7/2014 | Steinberg ............... | A61B 6/481 |
| | | | 382/199 |
| 8,781,197 B2 | 7/2014 | Wang et al. | |
| 8,805,471 B2 * | 8/2014 | Sakuragi ............... | G06T 7/0012 |
| | | | 600/407 |
| 8,927,288 B2 | 1/2015 | Hallahan et al. | |

(Continued)

FOREIGN PATENT DOCUMENTS

EP 3005289 B1 7/2017

OTHER PUBLICATIONS

Written Opinion and International Search Report for PCT Application No. PCT/US2020/066286 dated Mar. 16, 2021.

(Continued)

*Primary Examiner* — Tsung Yin Tsai

(57) ABSTRACT

Methods, devices and storage media for data processing are provided. One of the methods include: obtaining a target image, wherein the target image comprises at least one tubular image; determining a spatial distribution feature and an image feature of each of the at least one tubular image; obtaining, based on a tubular structure recognition model, at least one fusion feature respectively corresponding to the at least one tubular image by fusing the spatial distribution feature and the image feature of each of the at least one tubular image; and recognizing, based on the tubular structure recognition model and the at least one fusion feature respectively corresponding to the at least one tubular image, at least one tubular structure respectively corresponding to the at least one tubular image.

17 Claims, 5 Drawing Sheets

(56) References Cited

U.S. PATENT DOCUMENTS

| | | | |
|---|---|---|---|
| 9,364,167 | B2 | 6/2016 | Vertikov |
| 9,404,869 | B2 | 8/2016 | Keller |
| 9,920,188 | B2 | 3/2018 | Vogt et al. |
| 9,968,903 | B2 | 5/2018 | Hess et al. |
| 10,295,338 | B2 | 5/2019 | Abovitz et al. |
| 10,430,949 | B1* | 10/2019 | Wang ................... G06N 3/084 |
| 10,762,637 | B2* | 9/2020 | Gulsun ................. G06N 3/045 |
| 11,287,961 | B2* | 3/2022 | Gopinath ............. G16H 30/40 |
| 2006/0257006 | A1* | 11/2006 | Bredno ................. A61B 6/481 |
| | | | 382/128 |
| 2007/0165917 | A1* | 7/2007 | Cao ..................... G06T 7/0012 |
| | | | 382/128 |
| 2008/0187199 | A1* | 8/2008 | Gulsun ................. G06T 7/181 |
| | | | 382/173 |
| 2009/0041315 | A1 | 2/2009 | Fahmi et al. |
| 2010/0296709 | A1* | 11/2010 | Ostrovsky-Berman .................. |
| | | | G06T 7/162 |
| | | | 382/128 |
| 2012/0230565 | A1* | 9/2012 | Steinberg ............. G06T 5/001 |
| | | | 382/128 |
| 2014/0112566 | A1* | 4/2014 | Steinberg .............. A61B 34/10 |
| | | | 382/131 |
| 2016/0282432 | A1 | 9/2016 | Wang |
| 2018/0141274 | A1 | 5/2018 | Fink et al. |
| 2019/0130578 | A1* | 5/2019 | Gulsun ................. G06N 3/045 |
| 2019/0180153 | A1 | 6/2019 | Buckler et al. |
| 2019/0325579 | A1* | 10/2019 | Wang ................... G06T 7/174 |
| 2020/0020435 | A1* | 1/2020 | An ....................... G06T 7/0012 |
| 2020/0214571 | A1 | 7/2020 | Bradbury et al. |
| 2021/0169349 | A1* | 6/2021 | Madabhushi ............ A61B 5/08 |
| 2022/0148286 | A1* | 5/2022 | Keshwani ........... G06V 10/774 |

OTHER PUBLICATIONS

Wolterink et al., "Graph Convolutional Networks for Coronary Artery Segmentation in Cardiac CT Angiography," Cornell University Library, Aug. 14, 2019.

Extended European Search Report for European Application No. 20904762.0 dated Jun. 6, 2023.

"Image segmentation," Wikipedia, https://en.wikipedia.org/w/index.php?title=Image_segmentation&oldid=928378546, Nov. 28, 2019.

"Artificial neural network," Wikipedia, https://en.wikipedia.org/w/index.php?title=Artificial_neural_network&oldid=931851914, Dec. 21, 2019.

Wolterink et al., "Graph Convolutional Networks for Coronary Artery Segmentation in Cardiac CT Angiography," 16th European Conference—Computer Vision—ECCV 2020, Nov. 14, 2019.

* cited by examiner

DATA PROCESSING METHOD, EQUIPMENT AND STORAGE MEDIUM

CROSS-REFERENCE TO RELATED APPLICATION

This application is based on and claims priority to and benefit of Chinese Patent Application No. 201911357874.1, filed with the China National Intellectual Property Administration on Dec. 25, 2019, and entitled "DATA PROCESSING METHOD, EQUIPMENT AND STORAGE MEDIUM." The entire content of the above-identified application is incorporated herein by reference in its entirety.

TECHNICAL FIELD

This application relates to the field of computer technologies, and in particular, to a data processing method and device and a storage medium.

BACKGROUND

Computer-aided diagnosis (CAD) technologies may help physicians find lesions based on powerful capabilities of a computer in analysis and calculation, in combination with imaging, medical image processing technologies, and other possible physiological and biochemical means.

For example, in the treatment of vascular diseases, angiography may be performed based on Computed Tomography technologies to obtain an angiographic image, and then the distribution of vessels (or referred to as blood vessels) on the angiographic image is recognized based on computer technologies, to improve lesion analysis efficiency.

However, existing technologies do not make full use of features included in an angiographic image during recognition of the angiographic image, resulting in relatively low accuracies of recognition results. Therefore, a new solution is needed.

SUMMARY

In multiple aspects of this application, a data processing method and device and a storage medium are provided to enhance recognition results for tubular images included in an image.

Embodiments of this application provide a data processing method, including: obtaining a to-be-processed image, where the to-be-processed image includes at least one tubular image; calculating at least one spatial distribution feature and image feature respectively corresponding to the at least one tubular image; and recognizing, according to the at least one respective spatial distribution feature and image feature of the at least one tubular image, at least one tubular structure respectively corresponding to the at least one tubular image.

The embodiments of this application further provide a data processing method, including: obtaining a to-be-processed image, where the to-be-processed image includes at least one tubular image; and inputting the to-be-processed image into a tubular structure recognition model, to obtain at least one recognition result respectively corresponding to the at least one tubular image, where output data of a feature calculation layer in the tubular structure recognition model includes: a portion of input data of the feature calculation layer and a calculation result of the feature calculation layer based on the input data.

The embodiments of this application further provide a data processing method, including: obtaining a to-be-processed image, where the to-be-processed image includes at least one tubular image; and inputting the to-be-processed image into a tubular structure recognition model, to obtain at least one recognition result respectively corresponding to the at least one tubular image, where output data of a first feature calculation layer in the tubular structure recognition model is obtained by superimposing, by the first feature calculation layer, a calculation result of the first feature calculation layer based on input data of the first feature calculation layer and at least one spatial distribution feature of the at least one tubular image; and input data of a second feature calculation layer located after the first feature calculation layer includes: fusion features obtained by fusing the output data of the first feature calculation layer and respective image features of the at least one tubular image.

The embodiments of this application further provide a data processing method, including: obtaining a to-be-processed image, where the to-be-processed image includes at least one tubular image; and inputting the to-be-processed image into a tubular structure recognition model, to obtain at least one recognition result respectively corresponding to the at least one tubular image, where the tubular structure recognition model includes a graph convolutional networks (GCN), and input data of the GCN includes: a structure graph with respective features of the at least one tubular image as nodes.

The embodiments of this application further provide a data processing device, including a memory and a processor, where the memory is configured to store one or more computer instructions; and the processor is configured to execute the one or more computer instructions to perform steps in the data processing method provided in the embodiments of this application.

The embodiments of this application further provide a computer-readable storage medium storing a computer program, where when executed, the computer program implements steps in the data processing method provided in the embodiments of this application.

The embodiments of this application further provide a computer-implemented method for data processing. The method includes: obtaining a target image, wherein the target image comprises at least one tubular image; determining a spatial distribution feature and an image feature of each of the at least one tubular image; obtaining, based on a tubular structure recognition model, at least one fusion feature respectively corresponding to the at least one tubular image by fusing the spatial distribution feature and the image feature of each of the at least one tubular image; and recognizing, based on the tubular structure recognition model and the at least one fusion feature respectively corresponding to the at least one tubular image, at least one tubular structure respectively corresponding to the at least one tubular image.

The embodiments of this application further provide an apparatus for data processing. The apparatus comprises: one or more processors and one or more non-transitory computer-readable memories coupled to the one or more processors and configured with instructions executable by the one or more processors to cause the apparatus to perform operations comprising: obtaining a target image, wherein the target image comprises at least one tubular image; determining a spatial distribution feature and an image feature of each of the at least one tubular image; obtaining, based on a tubular structure recognition model, at least one fusion feature respectively corresponding to the at least one tubular image by fusing the spatial distribution feature and the image feature of each of the at least one tubular image; and recognizing, based on the tubular structure recognition model and the at least one fusion feature respectively corresponding to the at least one tubular image, at least one tubular structure respectively corresponding to the at least one tubular image.

The embodiments of this application further provide a non-transitory computer-readable storage medium configured with instructions executable by one or more processors to cause the one or more processors to perform operations comprising: obtaining a target image, wherein the target image comprises at least one tubular image; determining a spatial distribution feature and an image feature of each of the at least one tubular image; obtaining, based on a tubular structure recognition model, at least one fusion feature respectively corresponding to the at least one tubular image by fusing the spatial distribution feature and the image feature of each of the at least one tubular image; and recognizing, based on the tubular structure recognition model and the at least one fusion feature respectively corresponding to the at least one tubular image, at least one tubular structure respectively corresponding to the at least one tubular image.

In the data processing methods provided in the embodiments of this application, a tubular structure is recognized according to spatial distribution features and image features of tubular images included in a to-be-processed image, multiple complex features of tubular structures can be taken as a recognition basis, and a variety of different information of the tubular structures provided by the to-be-processed image can be fully used, which is conducive to improving recognition results of the tubular images.

BRIEF DESCRIPTION OF THE DRAWINGS

The accompanying drawings described herein are used to provide further understanding of this application and form a part of this application. Embodiments of this application and descriptions of the embodiments are used to explain this application and do not constitute undue limitations on this application. In the drawings.

DETAILED DESCRIPTION

In order to make the objectives, and advantages of this application clearer, the application will be described clearly in combination with embodiments and the corresponding accompanying drawings of this application. Clearly, the described embodiments are only a part rather than all of the embodiments of this application. All other embodiments obtained by a person of ordinary skill in the art based on the embodiments in this application without creative efforts fall within the protection of this application.

In existing technologies, during the recognition of an angiographic image, only partial information represented by the angiographic image is taken into account, and a variety of complex information included in a to-be-processed image is not fully used, thereby leading to relatively low accuracy of vascular recognition. The following is a brief description of defects of the existing technologies in combination with a naming method for coronary artery branches provided in the existing technologies. In the existing technologies, common naming methods for coronary artery branches are a registration-based method and a method based on tree structure and long short-term memory (LSTM) network.

In the registration-based method, main branches of a coronary tree, namely, a left coronary artery (LCA), a left main coronary artery (LM), a left anterior descending (LAD), and a left circumflex artery (LCX), are first recognized using a registration algorithm, and remaining branches are then categorized using rules and prior knowledge (for example, a topology of the coronary tree).

In the scheme based on tree structure and LSTM, a coronary tree is constructed into a binary tree, and each vessel is taken as a node of the binary tree. Then, a correlation between a parent node and child nodes is learned using an LSTM model, and finally a category of each node is predicted, so as to obtain a name of each vessel.

In the foregoing two schemes, only positional dependence of a main vessel and a branch vessel in a vascular tree is considered, but other information of vessels in the vascular tree is not fully considered. Therefore, fairly large errors exist in the results of naming vessels. The errors lead to especially more serious consequences when the main vessel is named incorrectly.

Figure 1:
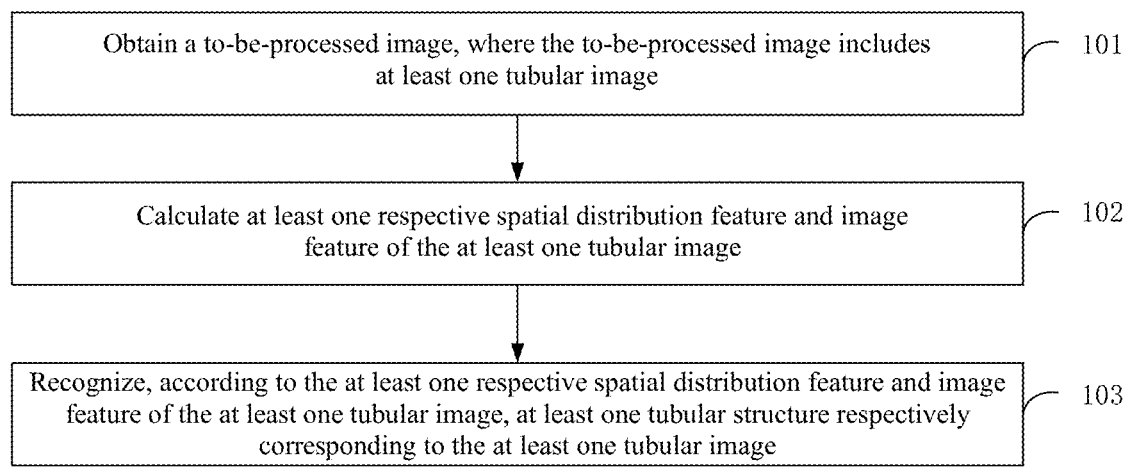
FIG. 1 is a schematic flowchart of a data processing method according to an embodiment of this application.

With respect to the foregoing technical problems in the existing technologies, embodiments of this application are provided to resolve the technical problems. The various embodiments of this application are described below in detail with reference to the accompanying drawings:

FIG. 1 is a schematic flowchart of a data processing method according to an embodiment of this application. As shown in FIG. 1, the method includes the following steps:

Step 101. Obtaining a to-be-processed image, where the to-be-processed image includes at least one tubular image.

Step 102. Calculating at least one respective spatial distribution feature and image feature of the at least one tubular image.

Step 103. Recognizing at least one tubular structure respectively corresponding to the at least one tubular image according to the at least one respective spatial distribution feature and image feature of the at least one tubular image.

The to-be-processed image may include an image obtained by imaging on the at least one tubular structure.

In some embodiments, the to-be-processed image may include: an angiographic image obtained by performing angiography on a tubular structure of an organism with the aid of a medical device. For example, the image may be a CT angiography (CTA) image of coronary arteries obtained by performing angiography on coronary arteries of an organism based on a CT technology.

In some other embodiments, the to-be-processed image may include: an image obtained by thermal imaging on hot water pipes laid in a city.

In some other embodiments, the to-be-processed image may include: remote sensing images obtained by remote sensing technology-based imaging on river channels, train tracks, highways, and the like distributed in a geographical environment. The to-be-processed image includes at least one tubular image. The tubular image refers to a corresponding image part on the to-be-processed image after angiography of the tubular structure. In a situation of a good imaging result, one tubular image may correspond to one tubular structure for angiography. For example, the angiographic image obtained through angiography on an organism may include vascular images. The image obtained by thermal imaging on hot water pipes laid in a city may include hot water pipe images. The remote sensing image obtained by remote sensing imaging on river channels distributed in a geographical environment may include river channel images.

After the imaging of the tubular structure, features of the tubular structure may be reflected on corresponding tubular images. Therefore, the corresponding tubular structure may be recognized based on the features shown in the tubular images. Generally, the tubular structure has relatively complex spatial distribution features and individual differences. Take blood vessels (or referred to as vessels) as an example: the vessels are relatively complex in an organism. Vessels in each part of the organism include a main vessel and branch vessels derived from sides of the main vessel. After angiography, the main vessel and the branch vessels are roughly tree-like. On the whole, different vessels in the vascular tree have some spatial distribution features. For example, some branch vessels are located on a left side of the main vessel, and some branch vessels are located on a right side of the main vessel. Locally, shapes, sizes, and directions of different vessels vary in the vascular tree.

Based on the foregoing, in this embodiment, in recognizing the tubular images on the to-be-processed image, at least one respective spatial distribution feature and image feature of the tubular images may be obtained from the to-be-processed image. Based on the spatial distribution features and the image features, complex features of the tubular structure may be more comprehensively taken as a basis for recognizing the tubular images, which is conducive to a more accurate recognition of the tubular structure on the to-be-processed image.

The spatial distribution features of the tubular images may include, but are not limited to, position features and direction features of the tubular images on the to-be-processed image, a connection relationship between the tubular images, and the like. The image features of the tubular images may include, but are not limited to, shape features and size features of the tubular images and the like, which are not described in detail here.

In this embodiment, a tubular structure is recognized according to spatial distribution features and image features of tubular images included in a to-be-processed image, multiple complex features of the tubular structure can be taken as a recognition basis, and a variety of different information of the tubular structure provided by the to-be-processed image can be fully used, which is conducive to improving recognition results of the tubular images.

In the foregoing and the following embodiments of this application, the process of recognizing the tubular images may be implemented using a neural networks (NN)-based machine learning model. The NN may include one or more of a convolutional neural networks (CNN), a deep neural network (DNN), a graph convolutional networks (GCN), a recurrent neural network (RNN), and an LSTM, which is not limited to this embodiment.

For ease of description, a model for recognizing tubular images is described as a tubular structure recognition model in the following embodiments of this application. In some embodiments, to make full use of multiple features of the tubular images on the to-be-processed image, the tubular structure recognition model may be formed by a CNN, an LSTM, and a GCN, and is illustrated below with reference to FIG. 2a, FIG. 2b, and FIG. 2c.

Figure 2A:
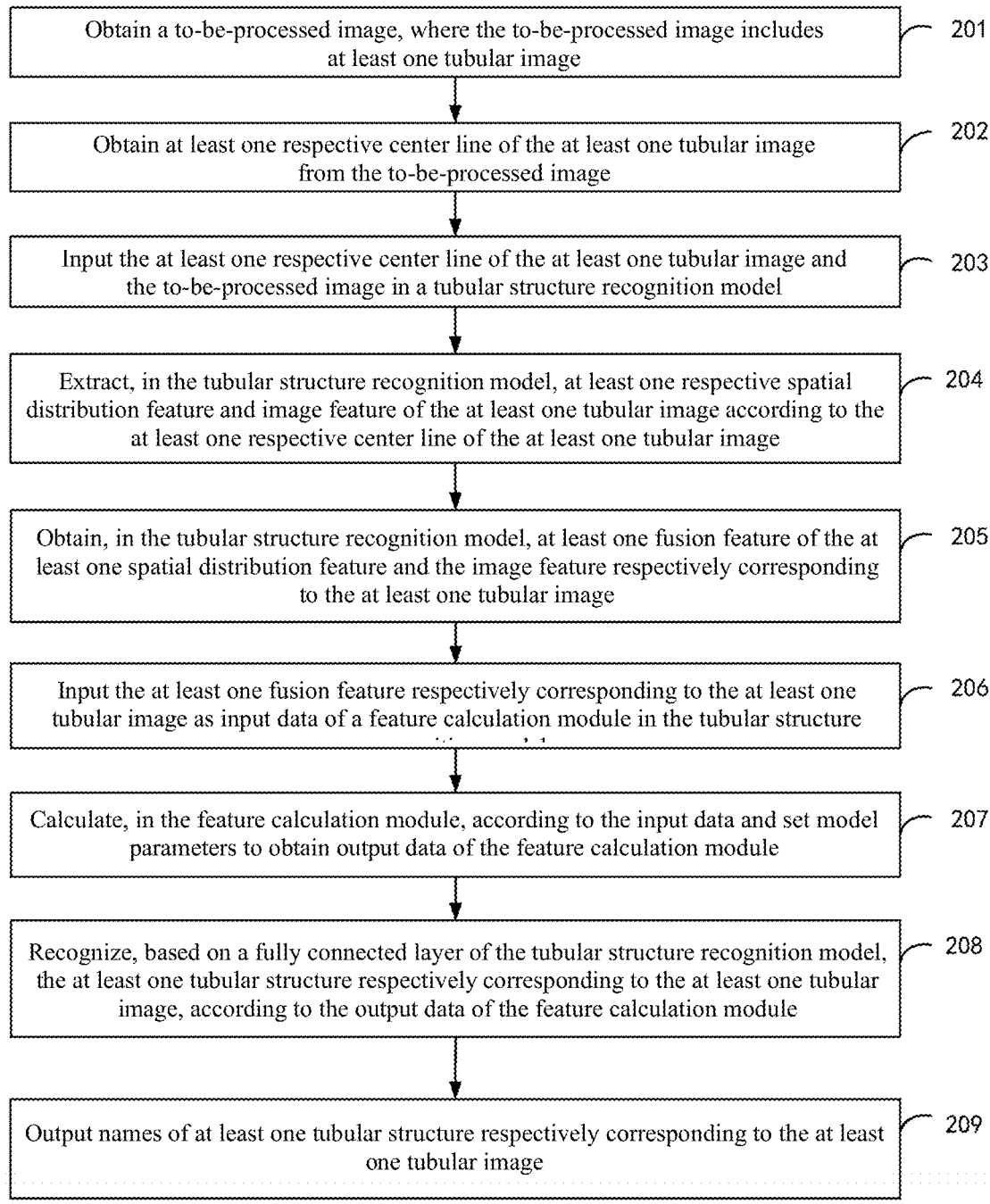
FIG. 2a is a schematic flowchart of a data processing method according to another embodiment of this application.

FIG. 2a is a schematic flowchart of a data processing method according to another embodiment of this application. As shown in FIG. 2a, the method includes the following steps:

Step 201. Obtaining a to-be-processed image, where the to-be-processed image includes at least one tubular image.

Step 202. Obtaining at least one respective center line of the at least one tubular image from the to-be-processed image.

Step 203. Inputting the at least one respective center line of the at least one tubular image and the to-be-processed image in a tubular structure recognition model.

Step 204. In the tubular structure recognition model, extracting at least one respective spatial distribution feature and image feature of the at least one tubular image according to the at least one respective center line of the at least one tubular image.

Step 205 In the tubular structure recognition model, obtaining at least one fusion feature of the at least one spatial distribution feature and the image feature respectively corresponding to the at least one tubular image.

Step 206. Inputting the at least one fusion feature respectively corresponding to the at least one tubular image as input data of a feature calculation module in the tubular structure recognition model.

Step 207. Calculating, in the feature calculation module, according to the input data and set model parameters to obtain output data of the feature calculation module.

Step 208. Recognizing at least one tubular structure respectively corresponding to the at least one tubular image, based on a fully connected layer of the tubular structure recognition model, according to the output data of the feature calculation module.

Step 209. Outputting name(s) of tubular structure(s) respectively corresponding to the at least one tubular image.

In step 201, the to-be-processed image includes at least one tubular image. For example, in some scenarios, when the to-be-processed image is implemented as a CT angiographic image of coronary arteries, the to-be-processed image may include multiple vascular images, and the multiple vascular images are in a tree-shaped distribution.

In step 202, take vessels as an example: the operation of obtaining center lines of the vascular images may be implemented based on vascular tracking.

During vascular tracking, a vascular tracker may be used to recognize a direction and a radius of a vessel at each position and perform iterative calculation to search for complete vessels. In this process, a vascular discriminator may be used to determine whether to terminate the search operation of the vascular tracker. Center lines of the vessels may be drawn based on the directions and radii of the vessels recognized by the vascular tracker and the vascular discriminator. The vascular tracker and the vascular discriminator may be implemented based on a multi-task three-dimensional (3D) CNN model, which are not described in detail here.

Next, in step 203, the at least one respective center line of the at least one tubular image extracted from the to-be-processed image may be inputted to the tubular structure recognition model.

In this embodiment, input of the tubular structure recognition model includes: the to-be-processed image and the at least one respective center line of the tubular images on the to-be-processed image. Output of the tubular structure recognition model includes: names of the tubular structures on the to-be-processed image. Based on the foregoing input and output, the tubular structure recognition model implements an "end-to-end" tubular image recognition operation. During the "end-to-end" recognition, the tubular structure recognition model does not adopt a calculation manner of first generating intermediate results and then obtaining a final recognition result according to the intermediate results, thereby effectively avoiding influences of the accuracies of the intermediate results on the accuracy of the final recognition result.

Figure 2B:
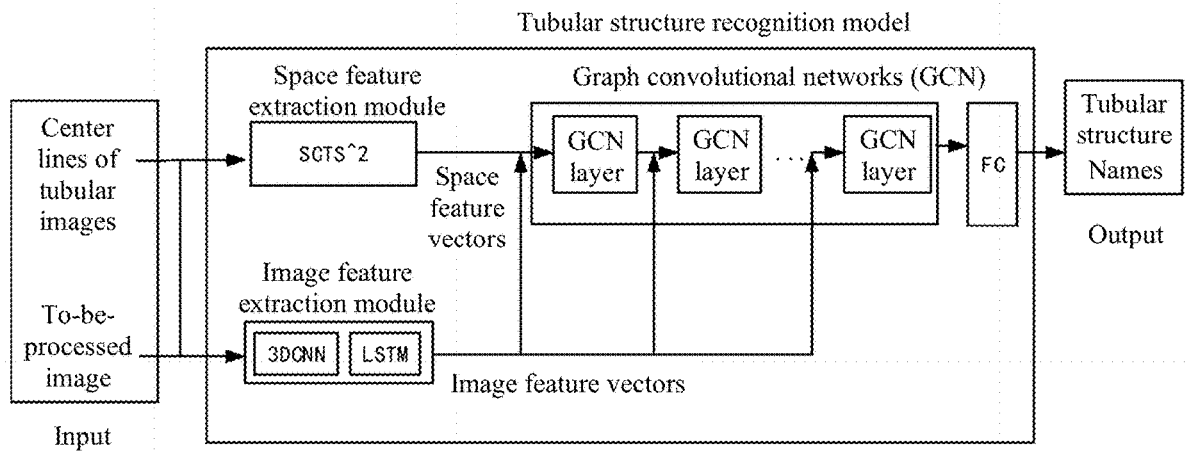
FIG. 2b is a schematic structural diagram of a tubular structure recognition model according to an embodiment of this application.

In step 204, a structure of the tubular structure recognition model may be as shown in FIG. 2b. Description is continued below with reference to FIG. 2b.

In some embodiments, the tubular structure recognition model may include a feature extraction module. The feature extraction module is configured to extract, according to the center line of each tubular image, the spatial distribution feature and the image feature of the each tubular image from the to-be-processed image.

In some embodiments, the feature extraction module included in the tubular structure recognition model may include: a spatial feature extraction module and an image feature extraction module.

The spatial feature extraction module is configured to extract the spatial distribution image of each tubular image. The image feature extraction module is configured to extract the image feature of the each tubular image. As shown in FIG. 2b, in some embodiments, the spatial feature extraction module may be implemented based on a spherical coordinate transform (SCTS^2) module. The image feature extraction module is implemented based on a 3DCNN and an LSTM network. In other embodiments, the spatial feature extraction module and the image feature extraction module may also be implemented by other algorithm modules, which are not limited in this embodiment.

Execution logic of the spatial feature extraction module and execution logic of the image feature extraction module are illustrated respectively below by taking a first tubular image in the at least one tubular image as an example. The first tubular image is any of the at least one tubular image.

A manner in which the spatial feature extraction module extracts spatial distribution features is implemented mainly based on a center line of a tubular image. The center line of the tubular image is formed by a series of 3D coordinate points in a spatial rectangular coordinate system (also referred to as a Cartesian coordinate system). In some embodiments, the spatial feature extraction module may obtain position coordinates of a starting point, an end point, and at least one middle point on a center line of the first tubular image, and generate a position feature vector of the first tubular image according to the position coordinates of the points.

During generation of the position coordinates, the spatial feature extraction module may perform coordinate transformation according to the obtained position coordinates of the points, and map the position coordinates of the points from the spatial rectangular coordinate system to a spherical coordinate system.

Description is provided below in combination with a point P (x, y, z) on the center line of the first tubular image, where (x, y, z) is a 3D coordinate of the point P in a spatial rectangular coordinate system XYZ.

Spherical coordinate transformation may be performed for P (x, y, z) according to formula (1):

$$\begin{aligned} x &= r\sin\theta\cos\varphi & r &= \sqrt{x^2 + y^2 + z^2} \\ y &= r\sin\theta\sin\varphi & \cos\theta &= z/r, \theta \in [0,\pi] \\ z &= r\cos\theta & \sin\varphi &= x/(r\sin\theta), \cos\varphi = y/(r\sin\theta) \end{aligned} \quad (1)$$

Coordinates of the point P in the spherical coordinate system may be obtained based on the formula 1. If described by matrix, the point P may be expressed as a matrix M of 2×2, $$M = \begin{bmatrix} \sin\theta & \sin\varphi \\ \cos\theta & \cos\varphi \end{bmatrix}.$$

After a coordinate matrix corresponding to a starting point, an end point, and at least one middle point on a center line of a tubular image is obtained, a position feature vector corresponding to the tubular image may be obtained.

In some embodiments, still taking the first tubular image as an example: the spatial feature extraction module may further calculate, based on the position coordinates of the starting point and the position coordinates of the end point on the center line of the first tubular image, a tangent vector of the starting point and a vector from the starting point to the end point. The spatial feature extraction module may obtain a direction feature vector of the first tubular image based on the tangent vector of the starting point and the vector from the starting point to the end point.

In some embodiments, the spatial feature extraction module may obtain a connection relationship between the at least one tubular image according to an association relation between position coordinates of points on at least one respective center line of the at least one tubular image. Take the first tubular image as an example: the spatial feature extraction module may extract the position coordinates of the starting point of the first tubular image, and then determine whether the position coordinates of the starting point coincide with position coordinates of a point on a center line of another tubular image. If the position coordinates of the starting point coincide with the position coordinates of the point on the center line of the another tubular image, it may be deemed that the first tubular image is connected to the another tubular image.

The spatial feature extraction module may take a combination of one or more of the position feature vector, the direction feature vector, and the connection relationship as the spatial distribution feature of the tubular image, which is not limited in this embodiment.

In some embodiments, the image feature extraction module may extract, from the to-be-processed image, at least one image region respectively corresponding to the at least one tubular image according to the at least one respective center line of the at least one tubular image. For example, take a first tubular image as an example: on the to-be-processed image, the image feature extraction module may extract, along a center line of the first tubular image, a series of bounding volumes as an image region corresponding to the first tubular image. A bounding volume may be a cube or a cylinder, and a cross-sectional size of the bounding volume accommodates the diameter of the first tubular image. For example, the cross-sectional size of the bounding volume may be slightly greater than the diameter of the first tubular image or equal to the diameter of the tubular image, which is not described in detail here.

After the at least one image region respectively corresponding to the at least one tubular image is obtained, the image feature extraction module may perform feature extraction on the at least one image region respectively corresponding to the at least one tubular image by using a CNN and an LSTM network, to obtain at least one image feature vector respectively corresponding to the at least one tubular image. When the tubular image is a 3D image, the CNN is implemented as a 3DCNN, for example, the 3DCNN shown in FIG. 2b, to perform feature extraction on the 3D tubular image.

In step 205, after the spatial distribution feature and the image feature of each tubular image are obtained, the tubular structure recognition model may fuse the spatial distribution feature and the image feature of the each tubular image, to obtain a fusion feature of the each tubular image. The process of obtaining fusion features is illustrated below still by taking the first tubular image as an example.

In some embodiments, when a spatial distribution feature and an image feature of the first tubular image are represented in a vector form, the tubular structure recognition model may splice a vector corresponding to the spatial distribution feature of the first tubular image and a vector corresponding to the image feature of the first tubular image, to obtain a feature-splicing vector of the first tubular image. The feature-splicing vector may be used to represent a fusion feature of the first tubular image.

For example, following step 204, the spatial distribution feature of the first tubular image includes a position feature vector and a direction feature vector, and the image feature is represented by an image feature vector. Then, the tubular structure recognition model may splice the position feature vector, the direction feature vector, and the image feature vector of the first tubular image, to obtain a feature-splicing vector of the first tubular image.

Feature fusion by vector splicing is an example manner of feature fusion. This application includes, but is not limited to, this manner. For example, in some other embodiments, when the spatial distribution feature and the image feature of the first tubular image are fused, the vector corresponding to the spatial distribution feature of the first tubular image and the vector corresponding to the image feature may be superimposed, which is not described in detail here.

Next, in step 206, the at least one fusion feature respectively corresponding to the at least one tubular image is inputted to a feature calculation module in the tubular structure recognition model. The feature calculation module refers to a module in the tubular structure recognition model, configured to extract features from input data according to set model parameters, for example, a convolution module in the CNN. In some embodiments, when the tubular structure recognition model is implemented as the structure shown in FIG. 2b, the feature calculation module may be implemented as a graph convolution module in the GCN.

The GCN has good learning performance for graph structure data, and is suitable for processing features of tubular images with spatial structure features. Therefore, to make full use of the advantages of the GCN, the tubular structure recognition model may further perform, before inputting the at least one fusion feature respectively corresponding to the at least one tubular image to a graph convolution module, the following operations, that is, structuring, according to spatial structure features of the at least one tubular image, the at least one fusion feature respectively corresponding to the at least one tubular image, to obtain graph structure data as input data of the graph convolution module. Based on this, the graph convolution module may further make full use of structure features reflected in the tubular images, which is conducive to further improving reliability and availability of the features extracted by the graph convolution module.

Based on the description of the foregoing steps, the at least one spatial distribution feature of the at least one tubular image obtained by the tubular structure recognition model may include a connection relationship between the at least one tubular image. Based on this, the tubular structure recognition model may generate (such as draw) a structure graph according to the connection relationship between the at least one tubular image by taking the at least one fusion feature respectively corresponding to the at least one tubular image as nodes; and take the structure graph as the input data of the graph convolution module. The structure graph is graph structure data, which may not only reflect the connection relationship of the fusion features of the at least one tubular image, but also include the fusion features of the at least one tubular image. Embodiments for obtaining the structure graph are illustrated below with reference to the accompanying drawings by taking an example of the tubular image being implemented as a vascular image.

Figure 2C:
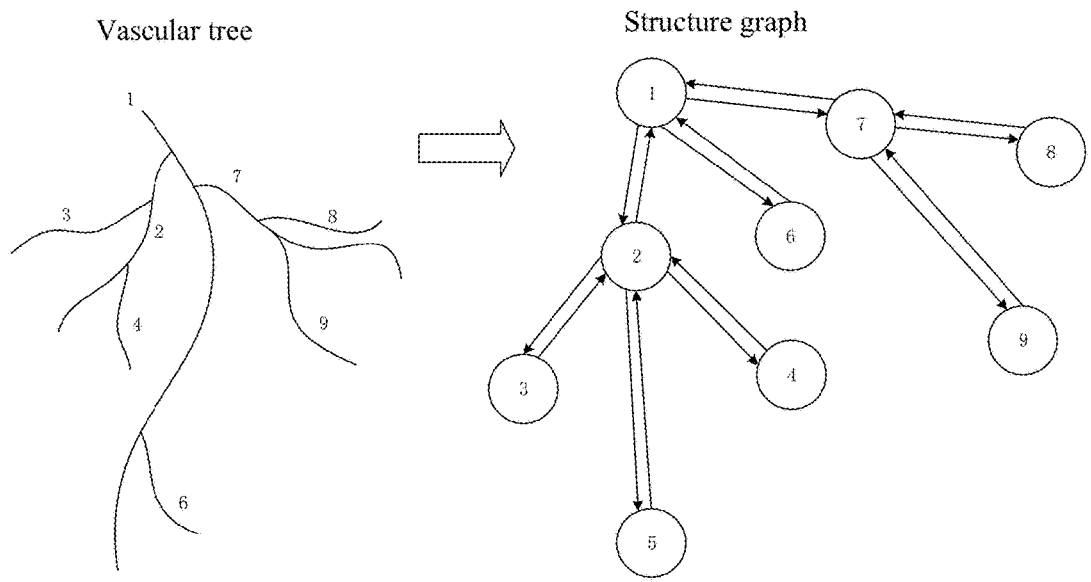
FIG. 2c is a schematic structural diagram of a structure graph according to an embodiment of this application.

FIG. 2c illustrates a structure graph obtained by drawing according to a connection relationship between vascular images in a vascular tree. In FIG. 2c, a node is a fusion feature of each vascular image in the vascular tree. If a connection relationship exists between two vascular images, fusion features corresponding to the two vascular images may be connected using a line segment. For example, in the vascular tree, a main vessel 1 is connected to a branch vessel 3 and a branch vessel 7. In the structure graph, correspondingly, a line segment may be added between a fusion feature of the main vessel 1 and a fusion feature of the branch vessel 3, and a line segment may be added between the fusion feature of the main vessel 1 and a fusion feature of the branch vessel 7. In step 207, the graph convolutional module may include multiple GCN layers, as shown in FIG. 2b. The quantity of the GCN layers may be set according to actual requirements, which may be set to, for example, 3, 4, 5, or the like, and is not limited in this embodiment.

Processing logic of the GCN layers is illustrated below by taking a first GCN layer in the multiple GCN layers as an example. The first GCN layer is any GCN layer in the graph convolutional module. The "first" used here for qualification is only for the convenience of description and distinction, and does not restrict an arrangement order or rank.

In the graph convolutional module, input of each GCN layer is graph structure data, and output is also graph structure data. That is, each GCN layer may perform a feature extraction operation on an inputted structure graph, and output the structure graph obtained after the operation, to transmit the structure graph to a next layer. For ease of description, graph structure data inputted to the first GCN layer is described as a first structure graph.

In some embodiments, if the first GCN layer is an initial GCN layer in the graph convolutional module, the first structure graph is the structure graph included in the input data of the graph convolutional module, that is, the structure graph drawn in the previous steps according to the fusion features of the at least one tubular image and the connection relationship between the at least one tubular image. In some embodiments, if the first GCN layer is not the initial GCN layer in the graph convolutional module, the first structure graph may be obtained according to a structure graph outputted by a previous GCN layer of the first GCN layer.

In the first GCN layer, the first structure graph may be updated according to a connection relationship between nodes in the first structure graph inputted to the first GCN layer and model parameters of the first GCN layer, to obtain a second structure graph.

The process of updating the first structure graph may be implemented as a process of updating a fusion feature of each node on the first structure graph. Illustration is provided below by taking a first node in the first structure graph as an example. The first node is any node on the first structure graph.

In some embodiments, for the first node, a second node connected to the first node may be obtained from the first structure graph. The quantity of the second node may be one or more, depending on different connections. Next, a feature fusion operation is performed on a fusion feature corresponding to the first node and one or more fusion features corresponding to the one or more second nodes, and the fusion feature corresponding to the first node is updated according to a feature obtained by the feature fusion operation.

For example, taking FIG. 2c as an example—nodes connected to a node 1 are: a node 2, a node 6, and a node 7. Next, an average value of a fusion feature corresponding to the node 1, a fusion feature corresponding to the node 2, a fusion feature corresponding to the node 6, and a fusion feature corresponding to the node 7 may be calculated, and the average value obtained by calculation is taken as a new fusion feature of the node 1.

In some embodiments, the manner in which the feature fusion operation is performed on the fusion feature corresponding to the first node and the one or more fusion features corresponding to the one or more second nodes may include: calculating an average of the fusion feature corresponding to the first node and the one or more fusion features corresponding to the one or more second nodes; or calculating, according to set weights, a weighted sum value of the fusion feature corresponding to the first node and the one or more fusion features corresponding to the one or more second nodes. This embodiment includes, but is not limited to, the manner.

Based on the foregoing manner, the fusion feature corresponding to each node on the first structure graph may be updated. After the update operation on the first structure graph is completed, the first GCN layer may obtain output data of the first GCN layer according to the model parameters of the first GCN layer and the second structure graph.

In some embodiments, a residual algorithm is introduced in GCN layers, to further improve an effect of transmission of features of tubular images between the GCN layers and improve the accuracy of recognition of tubular structures. In the residual algorithm, after performing a data processing operation of the GCN layer, each GCN layer may take processing results of the GCN layer and input data of the GCN layer as output data of the GCN layer. Illustration is provided below still in conjunction with the first GCN layer.

In some embodiments, when obtaining the output data of the first GCN layer according to the model parameters of the first GCN layer and the second structure graph, the first GCN layer may perform the following steps.

Firstly, feature extraction is performed on the second structure graph according to the model parameters of the first GCN layer, to obtain a third structure graph. Next, if the first GCN layer is an initial graph convolutional layer in the graph convolutional module, the at least one spatial distribution feature of the at least one tubular image and the third structure graph are superimposed, to serve as the output data of the first GCN layer; if the first GCN layer is not the initial graph convolutional layer, output data of a previous graph convolutional layer of the first GCN layer and the third structure graph may be superimposed, to serve as the output data of the first GCN layer.

Based on the foregoing, spatial distribution features of tubular images can be better transmitted between GCN layers with the deepening of the model.

On the basis of the introduction of the residual algorithm, the following steps may be further performed.

In some embodiments, input data of a next GCN layer may be formed by output data of a previous GCN layer and image features of the at least one tubular image, to further enhance an effect of transmission of image features of tubular images between the GCN layers and enhance the contribution of the image features to the tubular structure recognition process.

Still taking the first GCN layer as an example: In some embodiments, after the output data of the first GCN layer is obtained, feature fusion may be performed on the output data of the first GCN layer and the image features of the at least one tubular image, to serve as input data of the second GCN layer. The second GCN layer is a next GCN layer of the first GCN layer. In some embodiments, the feature fusion operation may be a vector splicing operation, which is not described in detail here.

The process of data transmission between the GCN layers is illustrated below by taking FIG. 2d as an example.

Figure 2D:
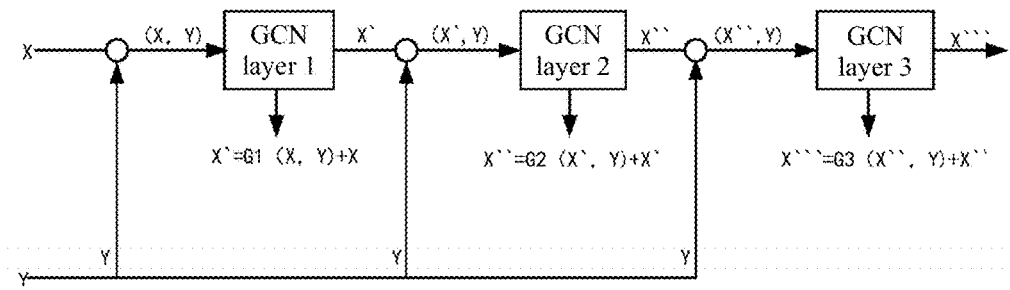
FIG. 2d is a schematic diagram of a data transmission process of a GCN layer according to an embodiment of this application.

In FIG. 2d, a circle may denote a vector splicing operation, X and Y denote a spatial distribution feature and an image feature of a tubular image respectively. The graph convolutional module includes three GCN layers: a GCN layer 1, a GCN layer 2, and a GCN layer 3.

A splicing vector (X, Y) obtained after splicing of X and Y is inputted to the graph convolutional module, that is, the input to the GCN layer 1 is (X, Y). If a calculation result of the GCN layer 1 based on (X, Y) is represented by G1(X, Y), output data of the GCN layer 1 is X'=G1(X, Y)+X.

Next, the output data X' of the GCN layer 1 is spliced with Y, to obtain a splicing vector (X, Y) which is inputted to the GCN layer 2. If a calculation result of the GCN layer 2 based on (X', Y) is represented by G2(X', Y), output data of the GCN layer 2 is X"=G1(X', Y)+.

Next, the output data X" of the GCN layer 2 is spliced with Y, to obtain a splicing vector (X", Y) which is inputted to the GCN layer 3. If a calculation result of the GCN layer 3 based on (X", Y) is represented by G3(X", Y), output data of the GCN layer 3 is X'''=G1(X", Y)+X".

In step 207, a calculation result of the graph convolutional module is transmitted to a fully connected layer in the tubular structure recognition model. On the fully connected layer, a probability that the at least one tubular image belongs to a known tubular structure may be calculated according to an output of the graph convolutional module, and at least one tubular structure respectively corresponding to the at least one tubular image are outputted according to the probability.

In this embodiment, a tubular structure is recognized according to spatial distribution features and image features of tubular images included in a to-be-processed image, multiple complex features of the tubular structure can be taken as an recognition basis, and a variety of different information of the tubular structure provided by the to-be-processed image can be fully used, which is conducive to improving recognition results of the tubular images.

For example, when the tubular structure is a vessel, a vessel on an angiographic image can be more accurately recognized based on the embodiments provided, which is conducive to improving the efficiency of lesion analysis.

Moreover, in this embodiment, a GCN is used in the tubular structure recognition model to process features of a vascular image, which may make full use of a spatial structure of a vessel during vascular recognition, reduces dependency of branch vessels on a main vessel, and reduces, to some extent, influences of a recognition result of the main vessel on recognition results of the branch vessels. In addition, a residual calculation manner is introduced in this embodiment, so that output data of each GCN layer includes input data of the GCN layer and a calculation result of the GCN layer based on the input data, which is conducive to effective transmission of features in the GCN layer and improvement of the accuracy of vascular recognition.

In some embodiments, after at least one vessel respectively corresponding to at least one vascular image on an angiographic image is recognized, at least one vessel name respectively corresponding to the at least one vascular image may be further displayed on the angiographic image, for a user to view a vascular recognition result.

In some embodiments, the user may modify the vascular recognition result according to an actual situation. For example, the user may double-click any of the at least one vascular image or any of the vessel names to initiate a name modification operation. In response to the name modification operation on any of the at least one vascular image, a modified vessel name may be obtained, and the modified vessel name may be displayed. In some embodiments, the modified vessel name may be taken as a true value of the tubular structure recognition model, to iteratively retrain the tubular structure recognition model to further optimize the tubular structure recognition model.

In some embodiments, an image obtained from an angiogram of one or more healthy vessels to which each vessel name belongs may be further obtained, to serve as a reference image. For example, vessel names of 3 angiograms included in an angiographic image are: an LCA, an LCX, and a LAD. Then, an angiographic image of the LCA, the LCX, and the LAD in a healthy state may be obtained, to serve as a reference image.

Next, the reference image and the at least one vascular image may be compared and displayed. Such a comparison and display manner may facilitate the user to quickly view whether there is an exception in the at least one angiographic image.

In some embodiments, a shape feature of a healthy vessel to which a vessel name belongs may be obtained based on the image obtained from the angiogram of the one or more healthy vessels to which each vessel name belongs. The shape feature may include a direction feature, a diameter feature, a wall thickness feature, and the like, which is not limited in this embodiment. Next, a shape feature of the at least one vascular image may be compared with the shape feature of the healthy vessel, and a vascular image in an abnormal state in the at least one vascular image may be determined according to a result of the comparison, to serve as a target vascular image.

Then, the target vascular image may be conspicuously displayed. In some embodiments, a manner in which the target vascular image is conspicuously displayed may include highlighting a target vessel, adding a star symbol to a target vessel, partially enlarging a target vessel, and selecting a target vessel for display, which is not limited in this embodiment. Based on such a manner, the user may be actively prompted for an exception, thereby improving the efficiency of the user for analysis on an angiographic image.

When the tubular structure recognition model used in the foregoing and the following embodiments of this application is configured for vascular recognition, a large number of angiographic images may be taken as training samples for model training based on the model structure illustrated in FIG. 2b. During the training, a loss function used may be a cross entropy loss function, which is not described in detail here.

Figure 3:
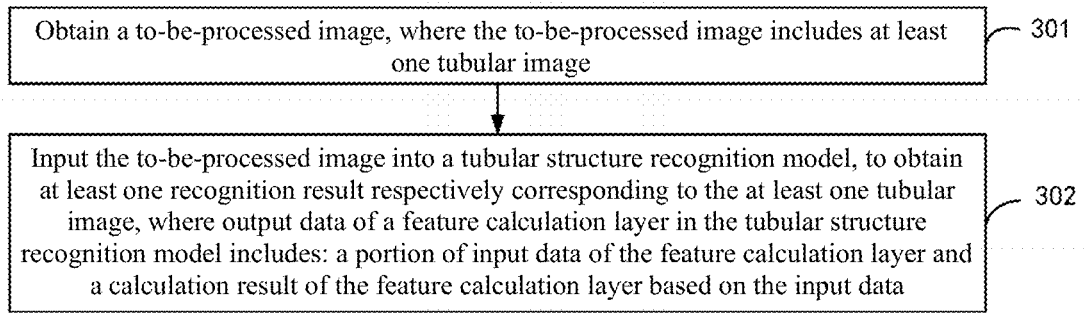
FIG. 3 is a schematic flowchart of a data processing method according to another embodiment of this application.

FIG. 3 is a schematic flowchart of a data processing method according to another embodiment of this application. As shown in FIG. 3, the method includes the following steps:

Step 301. Obtaining a to-be-processed image, where the to-be-processed image includes at least one tubular image.

Step 302. Inputting the to-be-processed image into a tubular structure recognition model, to obtain at least one recognition result respectively corresponding to the at least one tubular image, where output data of a feature calculation layer in the tubular structure recognition model includes: a portion of input data of the feature calculation layer and a calculation result of the feature calculation layer based on the input data.

In some embodiments, the tubular structure recognition model may include: one or more of a CNN, a DNN, a GCN, an RNN, and an LSTM, which is not limited in this embodiment.

In some embodiments, to make full use of image features and spatial distribution features of a tubular structure on the to-be-processed image, the tubular structure recognition model may be implemented as the structure shown in FIG. 2b. Correspondingly, the feature calculation layer may be implemented as the GCN layer shown in FIG. 2b.

In this embodiment, output data of the feature calculation layer includes a portion of input data of the feature calculation layer and a calculation result of the feature calculation layer based on the input data.

In some embodiments, if the feature calculation layer is an initial feature calculation layer, the portion of input data of the feature calculation layer is: at least one spatial distribution feature of the at least one tubular image; then, the output data of the feature calculation layer may include: the at least one spatial distribution feature of the at least one tubular image and a calculation result of the feature calculation layer based on the input data of the feature calculation layer.

If the feature calculation layer is not the initial feature calculation layer, the portion of input data of the feature calculation layer is: output data of a previous feature calculation layer. Then, the output data of the feature calculation layer may include: the output data of the previous feature calculation layer and a calculation result of the feature calculation layer based on the input data of the feature calculation layer.

In some embodiments, if the feature calculation layer is not the initial feature calculation layer, the input data of the feature calculation layer includes: fusion features obtained by fusing the output data of the previous feature calculation layer and respective image features of the at least one tubular image. Details may be obtained with reference to FIG. 2*d* and the description of the foregoing embodiments, which are not described in detail here.

Based on the foregoing, with gradual deepening of the model, data inputted to feature calculation layers and calculation result data of the feature calculation layers may be effectively transmitted between the feature calculation layers, which is conducive to improving the accuracy of tubular structure recognition.

Figure 4:
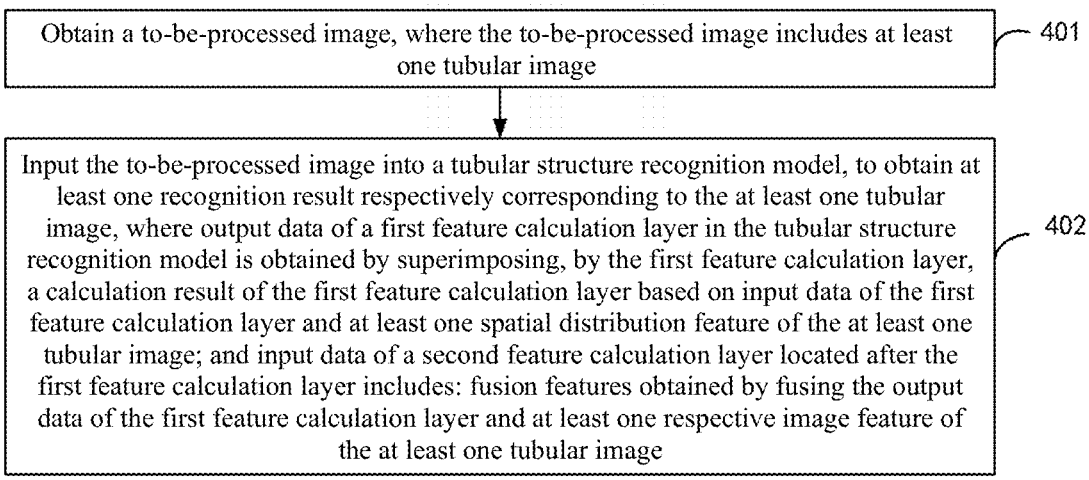
FIG. 4 is a schematic flowchart of a data processing method according to still another embodiment of this application.

FIG. 4 is a schematic flowchart of a data processing method according to another embodiment of this application. As shown in FIG. 4, the method includes the following steps:

Step 401. Obtaining a to-be-processed image, where the to-be-processed image includes at least one tubular image.

Step 402. Inputting the to-be-processed image into a tubular structure recognition model, to obtain at least one recognition result respectively corresponding to the at least one tubular image, where output data of a first feature calculation layer in the tubular structure recognition model is obtained by superimposing, by the first feature calculation layer, a calculation result of the first feature calculation layer based on input data of the first feature calculation layer and at least one spatial distribution feature of the at least one tubular image; and inputting data of a second feature calculation layer located after the first feature calculation layer includes: fusion features obtained by fusing the output data of the first feature calculation layer and at least one respective image feature of the at least one tubular image.

In some embodiments, the tubular structure recognition model includes a GCN; and the input data of the second feature calculation layer includes: a structure graph with the fusion features as nodes. Details may be obtained with reference to the description of the foregoing embodiments, which are not described in detail here.

In this embodiment, when output data of a previous feature calculation layer is inputted toward a next feature calculation layer, respective features of the at least one tubular image may be introduced to jointly serve as input data, which may further enhance an effect of transmission of image features of the at least one tubular image between GCN layers and enhance the contribution of the image features to the process of tubular structure recognition.

Figure 5:
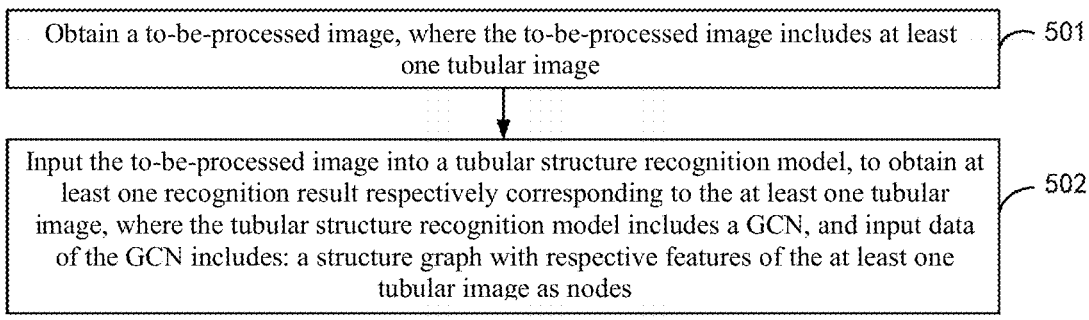
FIG. 5 is a schematic flowchart of a data processing method according to yet another embodiment of this application.

FIG. 5 is a schematic flowchart of a data processing method according to another embodiment of this application. As shown in FIG. 5, the method includes the following steps:

Step 501. Obtaining a to-be-processed image, where the to-be-processed image includes at least one tubular image.

Step 502. Inputting the to-be-processed image into a tubular structure recognition model, to obtain at least one recognition result respectively corresponding to the at least one tubular image, where the tubular structure recognition model includes a GCN, and input data of the GCN includes: a structure graph with respective features of the at least one tubular image as nodes.

In some embodiments, the features of the at least one tubular image include: at least one respective at least one spatial distribution feature of the at least one tubular image; or at least one respective image feature of the at least one tubular image; or at least one fusion feature of the at least one respective spatial distribution feature and image feature of the at least one tubular image.

In this embodiment, construction of a tubular structure recognition model based on a GCN may give full play to processing capabilities of the GCN for graph structure data, and make full use of spatial structure features of tubular images during tubular structure recognition, thereby further improving the accuracy of tubular structure recognition results.

The steps of each method provided in the foregoing embodiments may all be performed by the same device, or each method may also be performed by different devices. For example, step 201 to step 204 may be performed by a device A. In another example, step 201 and step 202 may be performed by a device A, step 203 may be performed by a device B, and so on.

Moreover, some of the processes described in the foregoing embodiments and the accompanying drawings include multiple operations occurring in some order. However, it should be clearly understood that, the operations may be performed not in the order in which the operations occur herein or performed in parallel. Serial numbers of the operations, such as 201 and 202, are only used to distinguish different operations, and the serial numbers do not represent any order of execution. In addition, the processes may include more or fewer operations, and the operations may be performed in order or performed in parallel.

It should be noted that, "first," "second," and other descriptions herein are used to distinguish different messages, devices, modules, and the like, and neither represent a sequence nor qualify "first" and "second" as different types.

Figure 6:
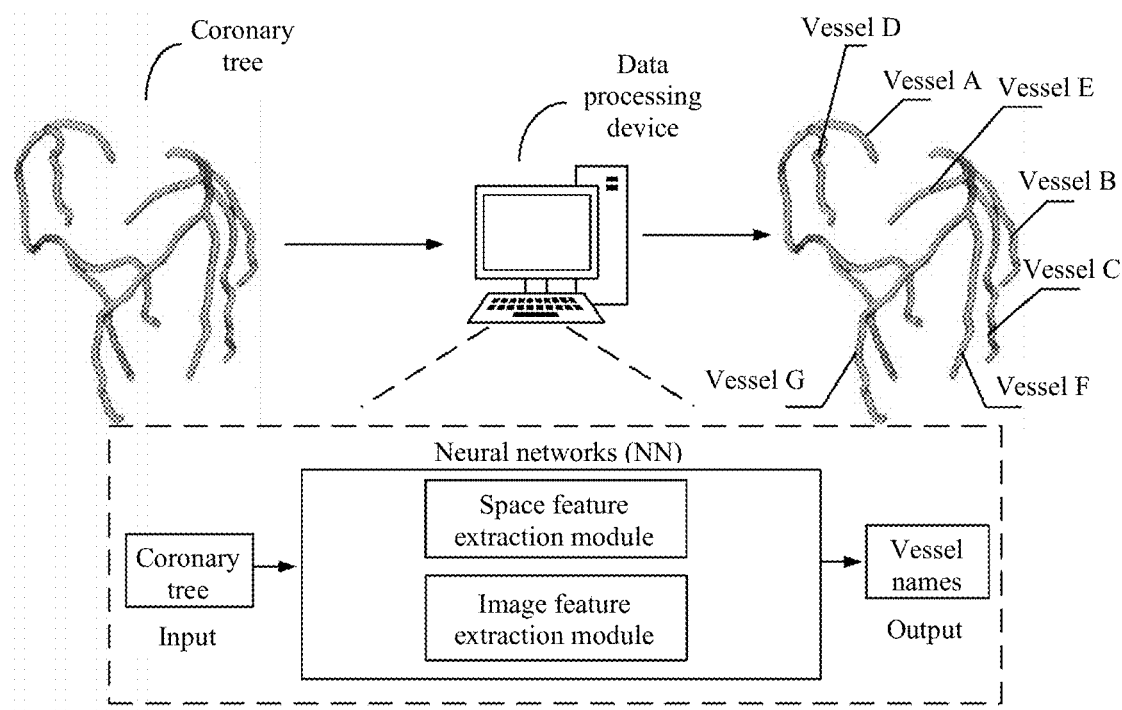
FIG. 6 is a diagram of an application scenario according to an embodiment of this application.

A typical application scenario of a data processing method according to an embodiment of this application is illustrated below with reference to FIG. 6.

The data processing methods according to the embodiments of this application may be applied to diagnosis of coronary heart disease. After a coronary angiographic image of a patient is obtained, the coronary angiographic image and a center line of a coronary tree may be inputted into a data processing device. The data processing device may perform the methods provided in the foregoing embodiments to recognize vessels on the coronary angiographic image, and output an image including vascular recognition results. The vascular recognition results include naming results of coronary artery branches, such as A to G shown in FIG. 6. Based on the naming results of coronary artery branches, a CAD system may reconstruct a coronary tree, detect and diagnose stenosis/plaque, and finally generate a diagnosis report. The diagnosis report may provide a doctor with additional information for the diagnosis of diseases, thereby improving the working efficiency of the doctor.

Figure 7:
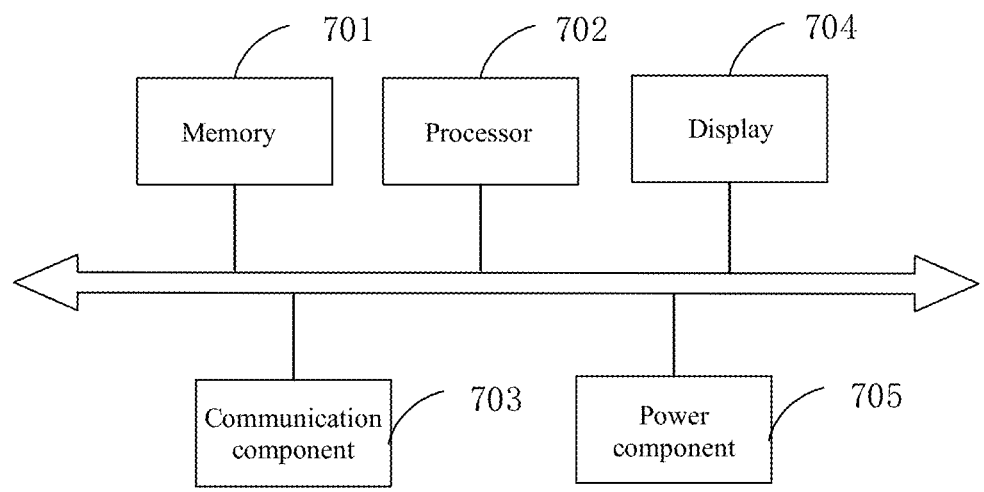
FIG. 7 is a schematic structural diagram of a data processing device according to an embodiment of this application.

FIG. 7 is a schematic structural diagram of a data processing device according to an embodiment of this application. As shown in FIG. 7, the data processing device includes: a memory 701 and a processor 702.

The memory 701 is configured to store computer instructions, and may be configured to store a variety of other data to support operations on a data processing device. For example, the data includes instructions for any application or method to operate on the data processing device, contact data, phonebook data, messages, images, videos, and the like.

The memory 701 may be implemented by any type of volatile or non-volatile storage device or a combination thereof, such as a static random access memory (SRAM), an electrically erasable programmable read-only memory (EE- PROM), an erasable programmable read-only memory (EPROM), a programmable read-only memory (PROM), a read-only memory (ROM), a magnetic memory, a flash memory, a magnetic disk, or an optical disk.

The processor 702 is coupled to the memory 701, and is configured to execute the computer program in the memory 701 to: obtain a to-be-processed image, where the to-be-processed image includes at least one tubular image; calculate at least one respective spatial distribution feature and image feature of the at least one tubular image; and recognize, according to the at least one respective spatial distribution feature and image feature of the at least one tubular image, at least one tubular structures respectively corresponding to the at least one tubular image.

In some embodiments, when calculating at least one respective spatial distribution feature and image feature of the at least one tubular image, the processor 702 is configured to: obtain, from the to-be-processed image, at least one respective center line of the at least one tubular image; and extract the at least one respective spatial distribution feature and image feature of the at least one tubular image according to the at least one respective center line of the at least one tubular image.

In some embodiments, for any of the at least one tubular image, when extracting the at least one respective spatial distribution feature and image feature of the at least one tubular image according to the at least one respective center line of the at least one tubular image, the processor 702 is configured to: generate, for any of the at least one tubular image, a position feature vector of the tubular image according to position coordinates of a starting point, an end point, and at least one middle point on the center line of the tubular image; obtain, for the tubular image, a direction feature vector of the tubular image according to a tangent vector of the starting point and a vector of the starting point pointing to the ending portion; and obtain a connection relationship between the at least one tubular image according to an association relation between position coordinates of points on the at least one respective center line of the at least one tubular image.

In some embodiments, when extracting the at least one respective spatial distribution feature and image feature of the at least one tubular image according to the at least one respective center line of the at least one tubular image, the processor 702 is configured to: extract, from the to-be-processed image, at least one image region respectively corresponding to the at least one tubular image according to the at least one respective center line of the at least one tubular image; and perform feature extraction on the at least one image region respectively corresponding to the at least one tubular image by using a CNN and an LSTM algorithm, to obtain at least one image feature vector respectively corresponding to the at least one tubular image.

In some embodiments, when recognizing, according to the at least one respective spatial distribution feature and image feature of the at least one tubular image, at least one tubular structures respectively corresponding to the at least one tubular image, the processor 702 is configured to: obtain, based on a tubular structure recognition model, fusion features of the spatial distribution features and the image features respectively corresponding to the at least one tubular image; take the at least one fusion feature respectively corresponding to the at least one tubular image as input data of a feature calculation module in the tubular structure recognition model; calculate, in the feature calculation module, according to the input data and set model parameters to obtain output data of the feature calculation module; and recognize, based on a fully connected layer of the tubular structure recognition model, the at least one tubular structure respectively corresponding to the at least one tubular image according to the output data of the feature calculation module.

In some embodiments, when obtaining fusion features of the spatial distribution features and the image features respectively corresponding to the at least one tubular image, the processor 702 is configured to: splice, for any of the at least one tubular image, a vector corresponding to a spatial distribution feature of the tubular image and a vector corresponding to an image feature of the tubular image, to obtain a feature-splicing vector of the tubular image; and obtain at least one feature-splicing vector respectively corresponding to the at least one tubular image as the at least one fusion feature respectively corresponding to the at least one tubular image.

In some embodiments, the tubular structure recognition model includes a GCN; and when taking the at least one fusion feature respectively corresponding to the at least one tubular image as input data of a feature calculation module in the tubular structure recognition model, the processor 702 is configured to: obtain a connection relationship between the at least one tubular image from the at least one spatial distribution feature of the at least one tubular image; draw a structure graph according to the connection relationship between the at least one tubular image by taking the at least one fusion feature respectively corresponding to the at least one tubular image as nodes; and take the structure graph as the input data of the feature calculation module.

In some embodiments, the feature calculation module includes multiple graph convolutional layers; and when calculating, in the feature calculation module, according to the input data and set model parameters to obtain output data of the feature calculation module, the processor 702 is configured to: update, based on a first graph convolutional layer in the multiple graph convolutional layers, a first structure graph according to an input connection relationship between nodes in the first structure graph, to obtain a second structure graph; and obtain output data of the first graph convolutional layer according to model parameters of the first graph convolutional layer and the second structure graph, where if the first graph convolutional layer is an initial graph convolutional layer, the first structure graph is the structure graph included in the input data; and if the first graph convolutional layer is not the initial graph convolutional layer, the first structure graph is obtained according to a structure graph outputted by a previous graph convolutional layer of the first graph convolutional layer.

In some embodiments, when updating a first structure graph according to an input connection relationship between nodes in the first structure graph, to obtain a second structure graph, the processor 702 is configured to: obtain, for a first node in the first structure graph, a second node connected to the first node from the first structure graph; perform a feature fusion operation on a fusion feature corresponding to the first node and a fusion feature corresponding to the second node; and update, according to a feature obtained after the feature fusion operation, the fusion feature corresponding to the first node.

In some embodiments, when obtaining output data of the first graph convolutional layer according to model parameters of the first graph convolutional layer and the second structure graph, the processor 702 is configured to: perform feature extraction on the second structure graph according to the model parameters of the first graph convolutional layer, to obtain a third structure graph; superimpose, if the first graph convolutional layer is an initial graph convolutional layer, the at least one spatial distribution feature of the at least one tubular image and the third structure graph, to serve as the output data of the first graph convolutional layer; and superimpose, if the first graph convolutional layer is not the initial graph convolutional layer, output data of a previous graph convolutional layer and the third structure graph, to serve as the output data of the first graph convolutional layer.

In some embodiments, after recognizing at least one tubular structure respectively corresponding to the at least one tubular image, the processor 702 is further configured to: display, on the angiographic image, at least one vessel name respectively corresponding to the at least one vascular image.

In some embodiments, the processor 702 is further configured to: obtain a modified vessel name in response to a name modification operation for any of the at least one vascular image; and display the modified vessel name, and optimizing the tubular structure recognition model according to the modified vessel name.

In some embodiments, the processor 702 is further configured to: obtain a reference image, wherein the reference image is obtained from an angiogram of at least one healthy vessel to which the at least one vessel name belongs; and compare and display the reference image and the at least one vascular image.

In some embodiments, the processor 702 is further configured to: obtain a shape feature of a healthy vessel to which one of the at least one the vessel name belongs; compare a shape feature of the at least one vascular image with the shape feature of the healthy vessel; determine, according to a result of the comparison, a target vascular image in an abnormal state in the at least one vascular image; and conspicuously display the target vascular image.

In some embodiments, the processor 702 is further configured to: perform feature fusion on the output data of the first graph convolutional layer and the image features of the at least one tubular image, to serve as input data of the second graph convolutional layer. The second graph convolutional layer is a next graph convolutional layer of the first graph convolutional layer.

Further, as shown in FIG. 7, the data processing device further includes: a communication component 703, a display 704, a power component 705, and other components. FIG. 7 illustrates only some components, which does not mean that the data processing device includes only the components shown in FIG. 7.

The communication component 703 is configured to facilitate wired or wireless communication between a device in which the communication component is located and other devices. The device in which the communication component is located may be connected to wireless networks based on communication standards, such as Wi-Fi, 2G, 3G, 4G, or 5G, or a combination thereof. In an embodiment, the communication component receives a broadcast signal or broadcast related information from an external broadcast management system via a broadcast channel. In an embodiment, the communication component may be implemented based on a near field communication (NFC) technology, a radio frequency recognition (RFID) technology, an infrared data association (IrDA) technology, an ultra-wideband (UWB) technology, a Bluetooth (BT) technology, and other technologies.

The display 704 includes a screen. The screen of the display may include a liquid crystal display (LCD) and a touch panel (TP). If the screen includes a TP, the screen may be implemented as a touch screen to receive an input signal from a user. The TP includes one or more touch sensors to sense touch, sliding, and gestures on the TP. The touch sensor(s) may not only sense a boundary of a touch or slide operation, but also detect duration and pressure associated with the touch or slide operation.

The power component 705 provides power for various components of a device in which the power component is located. The power component may include a power management system, one or more power sources, and other components associated with power generation, management, and distribution for the device in which the power component is located.

In this embodiment, the data processing device recognizes a tubular structure according to spatial distribution features and image features of tubular images included in a to-be-processed image, may take multiple complex features of the tubular structure as a recognition basis, and may make full use a variety of different information of the tubular structure provided by the to-be-processed image, which is conducive to improving recognition results of the tubular images, and improving the efficiency of lesion analysis.

The data processing device illustrated in FIG. 7, in addition to performing data processing operations according to the data processing logic described in the foregoing embodiments, may further perform the data processing operations according to data processing logic described below:

Execution logic 1: the processor 702 is configured to obtain a to-be-processed image, where the to-be-processed image includes at least one tubular image; and input the to-be-processed image into a tubular structure recognition model, to obtain at least one recognition result respectively corresponding to the at least one tubular image, where output data of a feature calculation layer in the tubular structure recognition model includes: a portion of input data of the feature calculation layer and a calculation result of the feature calculation layer based on the input data.

In some embodiments, if the feature calculation layer is an initial feature calculation layer, the portion of input data of the feature calculation layer is: at least one spatial distribution feature of the at least one tubular image; and if the feature calculation layer is not the initial feature calculation layer, the portion of input data of the feature calculation layer is: output data of a previous feature calculation layer.

In some embodiments, if the feature calculation layer is not the initial feature calculation layer, the input data of the feature calculation layer includes: fusion features obtained by fusing the output data of the previous feature calculation layer and respective image features of the at least one tubular image.

Execution logic 2: the processor 702 is configured to obtain a to-be-processed image, where the to-be-processed image includes at least one tubular image; and input the to-be-processed image into a tubular structure recognition model, to obtain at least one recognition result respectively corresponding to the at least one tubular image, where output data of a first feature calculation layer in the tubular structure recognition model is obtained by superimposing, by the first feature calculation layer, a calculation result of the first feature calculation layer based on input data of the first feature calculation layer and at least one spatial distribution feature of the at least one tubular image; and input data of a second feature calculation layer located after the first feature calculation layer includes: fusion features obtained by fusing the output data of the first feature calculation layer and respective image features of the at least one tubular image.

In some embodiments, the tubular structure recognition model includes a GCN; and the input data of the second feature calculation layer includes: a structure graph with the fusion features as nodes.

Execution logic 3: the processor 702 is configured to obtain a to-be-processed image, where the to-be-processed image includes at least one tubular image; and input the to-be-processed image into a tubular structure recognition model, to obtain at least one recognition result respectively corresponding to the at least one tubular image, where the tubular structure recognition model includes a GCN, and input data of the GCN includes: a structure graph with respective features of the at least one tubular image as nodes.

In some embodiments, the features of the at least one tubular image include: at least one respective at least one spatial distribution feature of the at least one tubular image; or at least one respective image features of the at least one tubular image; or at least one fusion features of the at least one respective spatial distribution feature and image feature of the at least one tubular image.

Correspondingly, embodiments of this application further provide a computer-readable storage medium storing a computer program. The computer program, when executed, can implement various steps, which may be executed by a data processing device, in the foregoing method embodiments.

Correspondingly, embodiments of this application further provide a computer-readable storage medium storing a computer program. The computer program, when executed, can implement various steps, which may be executed by a server, in the foregoing method embodiments.

A person skilled in the art should understand that the embodiments of this application may be provided as methods, systems, or computer program products. Therefore, this application may take the form of full hardware embodiments, full software embodiments, or an embodiment combining software and hardware aspects. Moreover, this application may take the form of a computer program product implemented on one or more computer-usable storage media (including, but not limited to, a disk memory, a compact disk read-only memory (CD-ROM), an optical memory, and the like) including computer-usable program code.

This application is described with reference to flowcharts and/or block diagrams of the method, device (system), and computer program product according to the embodiments of this application. Each process and/or block in the flowcharts and/or block diagrams and combinations of processes and/or blocks in the flowcharts and/or block diagrams may be implemented by computer program instructions. The computer program instructions may be provided to a processor of a general-purpose computer, a special-purpose computer, an embedded computer, or other programmable data processing devices to produce a machine, so that the instructions executed by the computer or the processors of other programmable data processing devices generate an apparatus configured to implement functions specified in one or more processes in the flowcharts and/or one or more blocks in the block diagrams.

The computer program instructions may also be stored in a computer-readable memory that can guide a computer or other programmable data processing devices to operate in some manner, so that the instructions stored in the computer-readable memory generate an article of manufacture including an instruction apparatus. The instruction apparatus implements the functions specified in one or more processes in the flowcharts and/or one or more blocks in the block diagrams.

The computer program instructions may also be installed onto a computer or other programmable data processing devices, so that a series of operational steps are performed on the computer or other programmable data processing devices to produce computer-implemented processing, and accordingly, the instructions executed on the computer or other programmable data processing devices provide steps for implementing the functions specified in one or more processes in the flowcharts and/or one or more blocks in the block diagrams.

In a typical configuration, a computing device includes one or more central processing units (CPUs), an input/output interface, a network interface, and a memory.

The memory may include a volatile memory, a random access memory (RAM), and/or a non-volatile memory, and other forms in a computer-readable medium, such as a ROM or a flash memory (flash RAM). The memory is an example of the computer-readable medium.

The computer-readable medium includes non-volatile and volatile media, and removable and non-removable media. Information storage may be implemented with any method or technology. Information may be a computer-readable instruction, a data structure, a module of a program, or other data. For example, a computer storage medium includes, but is not limited to, a phase-change random access memory (PRAM), a SRAM, a dynamic random access memory (DRAM), other types of RAMs, a ROM, an EEPROM, a flash memory or other memory technologies, a CD-ROM, a digital versatile disc (DVD) or other optical storages, a cassette tape, a magnetic tape/magnetic disk storage, or other magnetic storage devices, or any other non-transmission media, and may be used to store information accessible to the computing device. According to the description herein, the computer-readable medium does not include transitory computer-readable media (transitory media), such as modulated data signals and carriers.

It should be further noted that, the terms "include," "comprise," or any other variations thereof are intended to cover non-exclusive inclusion, so that a process, method, commodity, or device including a series of elements not only includes the elements, but also includes other elements not clearly listed, or further includes elements inherent to such a process, method, commodity, or device. In the absence of more limitations, an element defined by a statement "including a/an . . . " does not exclude that other identical elements further exist in the process, method, commodity, or device including the element.

The foregoing description includes embodiments of this application and is not intended to limit this application. For the person skilled in the art, this application may be subject to various modifications and changes. Any modifications, equivalent replacements, improvements, and the like made within the spirit and principle of this application should be encompassed in the scope of the claims of this application.

What is claimed is:

1. A computer-implemented method for data processing, comprising:

obtaining a target image, wherein the target image comprises at least one tubular image;

determining a spatial distribution feature and an image feature of each of the at least one tubular image;

obtaining, based on a tubular structure recognition model, at least one fusion feature respectively corresponding to the at least one tubular image by fusing the spatial distribution feature and the image feature of each of the at least one tubular image, wherein the tubular structure recognition model comprises a graph convolutional network (GCN) with multiple graph convolutional layers;

obtaining a connection relationship between the at least one tubular image from at least one spatial distribution feature of the at least one tubular image;

generating a first structure graph according to the connection relationship between the at least one tubular image;

inputting the first structure graph to a feature calculation module in the tubular structure recognition model as input data;

obtaining, according to the input data and model parameters of the feature calculation module, output data of the feature calculation module, wherein the obtaining the output data comprises:

updating, based on a first graph convolutional layer in the multiple graph convolutional layers, the first structure graph according to an input connection relationship between nodes in the first structure graph to obtain a second structure graph as the output data of the first graph convolutional layer; and recognizing at least one tubular structure respectively corresponding to the at least one tubular image according to the output data of the feature calculation module.

2. The method according to claim 1, wherein determining a spatial distribution feature and an image feature of each of the at least one tubular image comprises:

obtaining, from the target image, at least one respective center line of the at least one tubular image; and extracting the spatial distribution feature and image feature of each of the at least one tubular image according to the at least one respective center line of the at least one tubular image.

3. The method according to claim 2, wherein extracting the spatial distribution feature and image feature of each of the at least one tubular image according to the at least one respective center line of the at least one tubular image comprises at least one of the following:

generating, for any of the at least one tubular image, a position feature vector of the tubular image according to position coordinates of a starting point, an end point, and at least one middle point on the center line of the tubular image;

obtaining, for the tubular image, a direction feature vector of the tubular image according to a tangent vector of the starting point and a vector from the starting point to the end point; and obtaining a connection relationship between the at least one tubular image according to an association relation between position coordinates of points on the at least one respective center line of the at least one tubular image.

4. The method according to claim 2, wherein extracting the spatial distribution feature and image feature of each of the at least one tubular image according to the at least one respective center line of the at least one tubular image comprises:

extracting, from the target image, at least one image region respectively corresponding to the at least one tubular image according to the at least one respective center line of the at least one tubular image; and performing feature extraction on the at least one image region respectively corresponding to the at least one tubular image by using a convolutional neural networks (CNN) and a long short-term memory (LSTM) algorithm, to obtain at least one image feature vector respectively corresponding to the at least one tubular image.

5. The method according to claim 1, wherein obtaining, based on a tubular structure recognition model, at least one fusion feature respectively corresponding to the at least one tubular image by fusing the spatial distribution feature and the image feature of each of the at least one tubular image comprises:

splicing, for any of the at least one tubular image, a vector corresponding to a spatial distribution feature of the tubular image and a vector corresponding to an image feature of the tubular image, to obtain a feature-splicing vector of the tubular image; and obtaining at least one feature-splicing vector respectively corresponding to the at least one tubular image as the at least one fusion feature respectively corresponding to the at least one tubular image.

6. The method according to claim 1,
wherein the obtaining the output data further comprises:
obtaining the second structure graph outputted by the first graph convolutional layer;

updating, based on a second graph convolutional layer in the multiple graph convolutional layers, the second structure graph according to an input connection relationship between nodes in the second structure graph, to obtain a third structure graph; and obtaining output data of the second graph convolutional layer according to model parameters of the second graph convolutional layer and the third structure graph.

7. The method according to claim 6, wherein updating the second structure graph comprises:

obtaining, for a first node in the second structure graph, a second node connected to the first node from the second structure graph;

performing a feature fusion operation on a fusion feature corresponding to the first node and a fusion feature corresponding to the second node; and updating, according to a feature obtained after the feature fusion operation is performed, the fusion feature corresponding to the first node.

8. The method according to claim 6, wherein obtaining the output data of the second graph convolutional layer comprises:

performing feature extraction on the second structure graph according to the model parameters of the second graph convolutional layer, to obtain a third structure graph; and superimposing output data of the first graph convolutional layer and the third structure graph, to serve as the output data of the second graph convolutional layer.

9. The method according to claim 8, further comprising:
performing feature fusion on the output data of the second graph convolutional layer and the image features of the at least one tubular image, to serve as input data of a next graph convolutional layer.

10. The method according to claim 1, wherein the target image comprises: an angiographic image; and the at least one tubular image, comprising at least one vascular image, and wherein after recognizing the at least one tubular structure respectively corresponding to the at least one tubular image, the method further comprises:

displaying, on the angiographic image, at least one vessel name respectively corresponding to the at least one vascular image.

11. The method according to claim 10, further comprising:
obtaining a modified vessel name in response to a name modification operation for any of the at least one vascular image; and
displaying the modified vessel name, and optimizing the tubular structure recognition model according to the modified vessel name.

12. The method according to claim 10, further comprising:
obtaining a reference image from an angiogram of at least one healthy vessel to which the at least one vessel name belongs; and
comparing and displaying the reference image and the at least one vascular image.

13. The method according to claim 10, further comprising:
obtaining a shape feature of a healthy vessel to which one of the at least one vessel name belongs;
comparing a shape feature of the at least one vascular image with the shape feature of the healthy vessel;
determining, according to a result of the comparison, a target vascular image in an abnormal state in the at least one vascular image; and
displaying the target vascular image.

14. The method according to claim 1, wherein the tubular structure recognition model comprises a feature calculation layer, and output data of the feature calculation layer in the tubular structure recognition model comprises: a portion of input data of the feature calculation layer and a calculation result of the feature calculation layer based on the input data, and
wherein the feature calculation layer is an initial feature calculation layer, and the portion of input data of the feature calculation layer is: at least one spatial distribution feature of the at least one tubular image.

15. The method according to claim 1, wherein the tubular structure recognition model comprises a feature calculation layer, and output data of the feature calculation layer in the tubular structure recognition model comprises: a portion of input data of the feature calculation layer and a calculation result of the feature calculation layer based on the input data, and
wherein the feature calculation layer is not an initial feature calculation layer, and the portion of input data of the feature calculation layer is: output data of a previous feature calculation layer; and the input data of the feature calculation layer comprises: at least one fusion feature obtained by fusing the output data of the previous feature calculation layer and at least one image feature of the at least one tubular image.

16. An apparatus for data processing, comprising: one or more processors and one or more non-transitory computer-readable memories coupled to the one or more processors and configured with instructions executable by the one or more processors to cause the apparatus to perform operations comprising:
obtaining a target image, wherein the target image comprises at least one tubular image;
determining a spatial distribution feature and an image feature of each of the at least one tubular image;
obtaining, based on a tubular structure recognition model, at least one fusion feature respectively corresponding to the at least one tubular image by fusing the spatial distribution feature and the image feature of each of the at least one tubular image, wherein the tubular structure recognition model comprises a graph convolutional network (GCN) with multiple graph convolutional layers;
obtaining a connection relationship between the at least one tubular image from at least one spatial distribution feature of the at least one tubular image;
generating a first structure graph according to the connection relationship between the at least one tubular image;
inputting the first structure graph to a feature calculation module in the tubular structure recognition model as input data;
obtaining, according to the input data and model parameters of the feature calculation module, output data of the feature calculation module, wherein the obtaining the output data comprises:
updating, based on a first graph convolutional layer in the multiple graph convolutional layers, the first structure graph according to an input connection relationship between nodes in the first structure graph to obtain a second structure graph as the output data of the first graph convolutional layer; and
recognizing at least one tubular structure respectively corresponding to the at least one tubular image according to the output data of the feature calculation module.

17. A non-transitory computer-readable storage medium configured with instructions executable by one or more processors to cause the one or more processors to perform operations comprising:
obtaining a target image, wherein the target image comprises at least one tubular image;
determining a spatial distribution feature and an image feature of each of the at least one tubular image;
obtaining, based on a tubular structure recognition model, at least one fusion feature respectively corresponding to the at least one tubular image by fusing the spatial distribution feature and the image feature of each of the at least one tubular image, wherein the tubular structure recognition model comprises a graph convolutional network (GCN) with multiple graph convolutional layers;
obtaining a connection relationship between the at least one tubular image from at least one spatial distribution feature of the at least one tubular image;
generating a first structure graph according to the connection relationship between the at least one tubular image;
inputting the first structure graph to a feature calculation module in the tubular structure recognition model as input data;
obtaining, according to the input data and model parameters of the feature calculation module, output data of the feature calculation module, wherein the obtaining the output data comprises:
updating, based on a first graph convolutional layer in the multiple graph convolutional layers, the first structure graph according to an input connection relationship between nodes in the first structure graph to obtain a second structure graph as the output data of the first graph convolutional layer; and
recognizing at least one tubular structure respectively corresponding to the at least one tubular image according to the output data of the feature calculation module.

* * * * *